US00PP25534P3

(12) United States Plant Patent
Kardos

(10) Patent No.: US PP25,534 P3
(45) Date of Patent: May 12, 2015

(54) ***LOROPETALUM CHINENSE* VAR. *RUBRUM* PLANT NAMED 'PIILC-I'**

(50) Latin Name: ***Loropetalum chinense* var. *rubrum***
Varietal Denomination: PIILC-I

(71) Applicant: Plant Introductions, Inc., Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 136 days.

(21) Appl. No.: 13/694,190

(22) Filed: Nov. 5, 2012

(65) Prior Publication Data

US 2013/0174309 P1 Jul. 4, 2013

Related U.S. Application Data

(60) Provisional application No. 61/582,920, filed on Jan. 4, 2012.

(51) Int. Cl.
*A01H 5/00* (2006.01)

(52) U.S. Cl.
USPC ..... Plt./226

(58) Field of Classification Search
CPC ..... A01H 5/02; A01H 5/00
USPC ..... Plt./226, 263.1
See application file for complete search history.

(56) References Cited

U.S. PATENT DOCUMENTS

PP16,615 P2 6/2006 Griffith
PP18,441 P2 1/2008 Berry

OTHER PUBLICATIONS

Horticopia. *Loropetalum chinense* var. *rubrum* 'Crimson Fire', retrievd on Jun. 17, 2014, retrived from the Internet at <http://www.horticopia.com/hortpip/Plants/html/042/P20042.shtml> one page.*
Lakeshore Garden Centre. Crimson Fire Chinese Fringeflower, retrieved on Jun. 17, 2014, retrieved from the Internet at <http://www.horticopia.com/hortpip/Plants/html/042/P20042.shtml>2 pp.*
*Loropetalum* Catalog Page (distributed at a trade show Jan. 5, 2011) at that time named "*Loropetalum* 'Crimson Fire'", 1 pg.
Plant Introductions, Inc. webpage, (downloaded Dec. 30, 2011) "*Loropetalum* selections", http : www . plantintroductions.com/loropetalumselection . html , 2 pgs.

* cited by examiner

*Primary Examiner* — June Hwu
(74) *Attorney, Agent, or Firm* — Lathrop & Gage LLP

(57) ABSTRACT

A new and distinct cultivar of *Loropetalum chinense* var. *rubrum* plant named 'PIILC-I', characterized by its compact, mounded, spreading growth habit; rich, reddish purple foliage color that persists through summer and winter; bright pink flowers in spring; and improved cold hardiness compared to other compact purple-leaf cultivars.

3 Drawing Sheets

Genus and species of plant claimed: *Loropetalum chinense* var. *rubrum*.

Variety denomination: 'PIILC-I'.

BACKGROUND OF THE INVENTION

The present invention relates to a new and distinct cultivar of *Loropetalum chinense* var. *rubrum*, a member of the Hamamelidaceae family, hereinafter referred to by its cultivar name 'PIILC-I'. This cultivar is grown primarily as an ornamental for landscape use and for use as a potted plant.

The cultivar originated from an open-pollination of *Loropetalum chinense* var. *rubrum* 'GriffCRL' (U.S. Plant Pat. No. 16,615) in Watkinsville, Ga. in 2008, and was selected from the progeny seedlings of this cross by continued evaluation for growth habit and improved foliage characteristics. The cultivar 'PIILC-I' originated and was discovered in a cultivated environment in an outdoor nursery in Watkinsville, Ga.

'PIILC-I' has been asexually reproduced by softwood cuttings since 2009 in Watkinsville, Ga. The characteristics of the cultivar have been stable and reproduced true to type in successive vegetative generations.

SUMMARY OF THE INVENTION

'PIILC-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIILC-I' from all other varieties in commerce known to the inventor. 1) Compact, mounded, spreading growth habit. 2) Rich, reddish purple foliage color that persists through summer and winter. 3) Bright pink flowers in spring. 4) Improved cold hardiness compared to other compact purple-leaf cultivars.

'PIILC-I' is distinguished from its female parent 'GriffCRL' by its growth habit and foliage color. 'PIILC-I' has a compact mounded, spreading growth habit reaching 86 cm×211 cm after 4 years, whereas 'GriffCRL' has an overall larger, rounded growth habit reaching approximately 244 to 305 cm high and wide in the same amount of time. 'PIILC-I' has rich, reddish purple foliage that persists through summer and winter, whereas 'GriffCRL' has duller red-purple foliage that will become greenish purple in summer and winter. There are no other cultivars of Loropetalum chinense var. rubrum with this combination of traits known to the inventor.

'PIILC-I' can be compared to the cultivar 'Peack' (U.S. Plant Pat. No. 18,441), but differs in growth habit, overall size, vigor, and hardiness. 'PIILC-I' has a compact mounded, spreading growth habit reaching 86 cm×211 cm after 4 years, whereas 'Peack' has a mounding and weeping habit reaching 46 cm×92 cm after 3 years. 'PIILC-I' is more vigorous than 'Peack'. 'PIILC-I' has exhibited increased cold hardiness compared to 'Peack' in Zone 7.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Loropetalum.*

DETAILED DESCRIPTION

Figure 1:
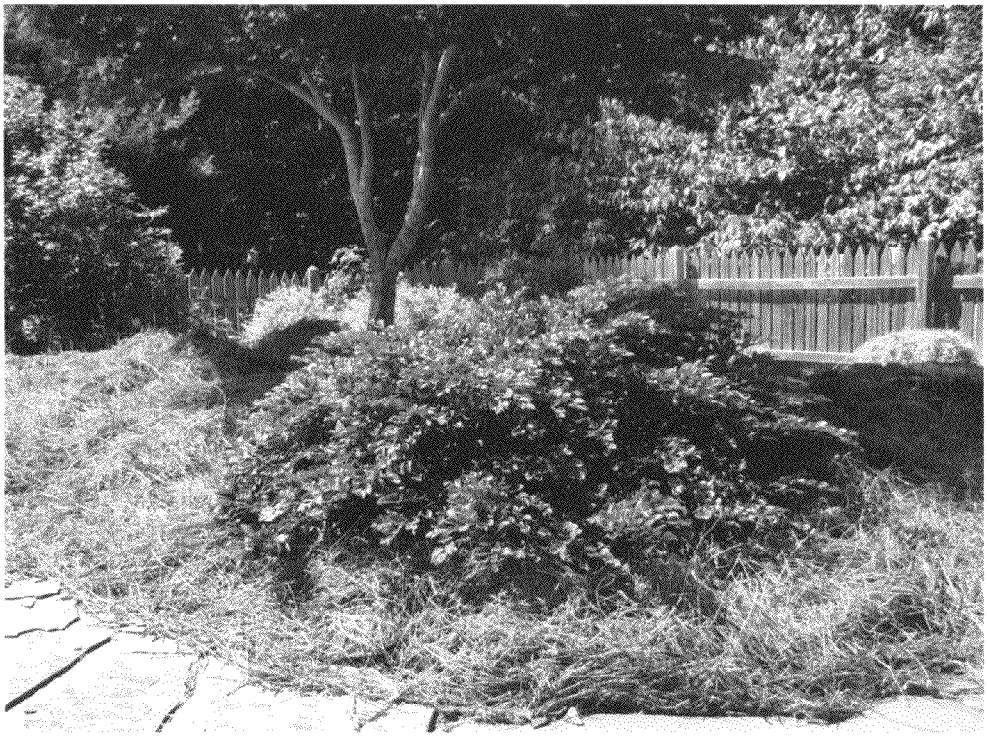
FIG. 1 illustrates the growth habit of a two-year-old 'PIILC-I' plant growing in the ground.
Figure 2:
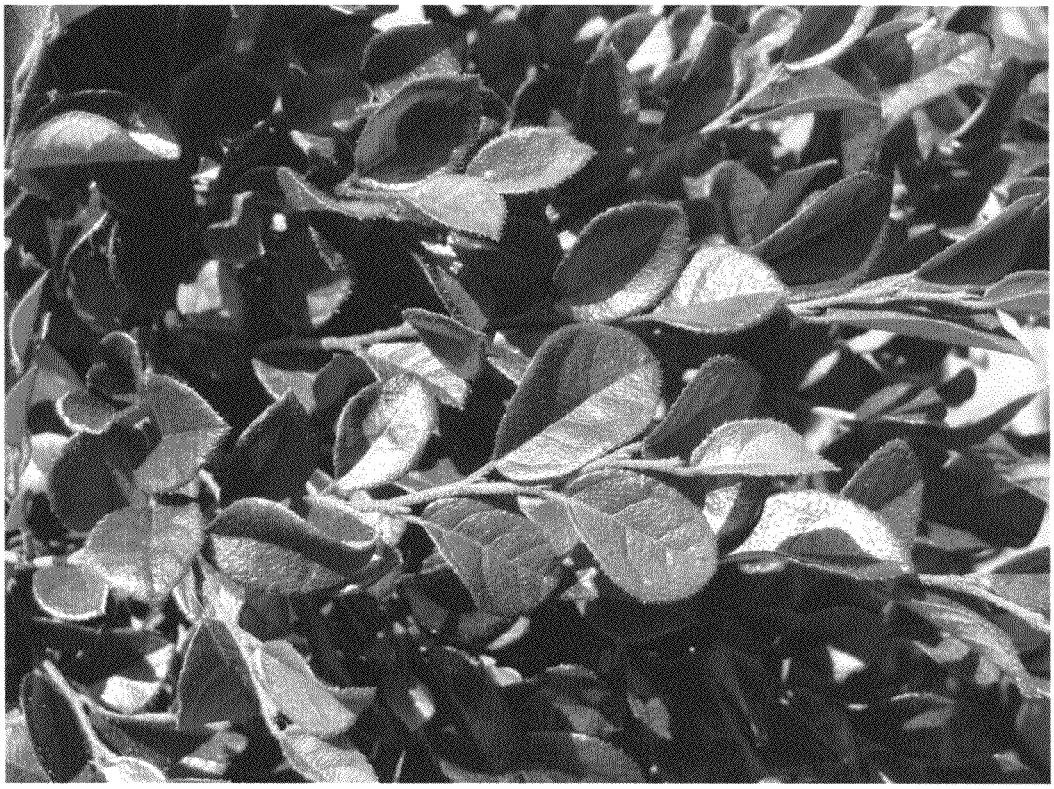
FIG. 2 illustrates a close-up of the foliage of a two-year-old 'PIILC-I' plant.
Figure 3:
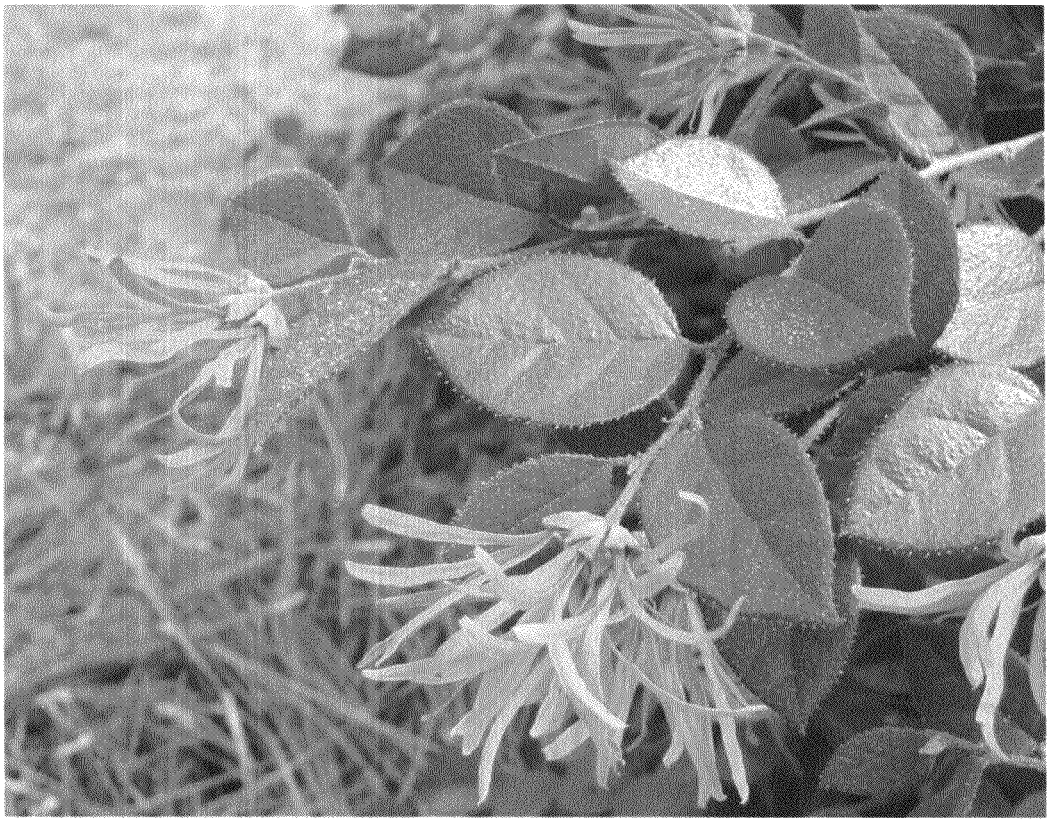
FIG. 3 illustrates a close-up of the flowers of a two-year-old 'PIILC-I' plant.

In the following description, color references are made to The Royal Horticultural Society Colour Chart, 2007 Edition, except where general terms of ordinary dictionary significance are used. Plants used for the description were approximately 2 and a half years old and were grown in 11.8 L containers under outdoor conditions in Watkinsville, Ga. Colors are described using The Royal Horticultural Society Colour Chart (R.H.S.).

Botanical classification: *Loropetalum chinense* var. *rubrum* 'PIILC-I'.

Parentage:

*Female, or seed, parent.*—*Loropetalum chinense* var. *rubrum* 'GriffCRL' (U.S. Plant Pat. No. 16,615).

*Male, or pollen, parent.*—Unknown (open-pollinated).

Propagation:

*Type cutting.*—Terminal cuttings.

*Time to initiate roots, summer.*—About 35 days at 32° C.

PLANT DESCRIPTION

Flowering evergreen shrub; compact, mounded, spreading growth habit. Freely branching; pruning enhances lateral branch development.

Root description: Numerous, fine, fibrous and well-branched.

Plant size: The original plant, now about 4-years-old in the ground, is about 86 cm in height from the soil level to the top of the foliage, and about 211 cm in diameter. First year stems have a length of about 20 cm. First year stems have a diameter of about 1.5 mm. Shape: round. Color: N186C. Pubescence: heavily stellate. Second year stems have a length of about 30 cm. Second year and older stems have a diameter of about 3 mm or more. Shape: round. Color: 165A. Pubescence: none.

Trunk diameter: About 1.3 cm at the soil line. Color: 199A.

Internode length: About 1.4 cm.

Strength: Flexible when young, more easily broken once mature.

Bark: Exfoliates in flakes beginning on second or third year stems 177B in color.

Vegetative buds: Alternate in arrangement, naked, with stellate pubescence.

*Shape.*—Ovoid.

*Color.*—N186C.

*Size.*—About 1 mm in length and 1 mm in width.

Foliage description:

*Arrangement.*—Alternate, simple.

*Length.*—About 2.7 cm.

*Width.*—About 2 cm.

*Shape.*—Ovate-rounded.

*Apex.*—Pointed.

*Base.*—Oblique.

*Margin.*—Entire with setose pubescence.

*Texture* (*upper and lower surfaces*).—Stellate or sandpaper like pubescence.

*Venation pattern.*—Pinnate.

*Venation color in developing foliage* (*upper and lower surfaces*).—187B.

*Venation color in fully expanded foliage* (*upper surface*).—N77A.

*Venation color in fully expanded foliage* (*lower surface*).—N77D.

*Color in developing foliage* (*upper and lower surfaces*).—187B.

*Color in fully expanded foliage* (*upper surface*).—N77A.

*Color in fully expanded foliage* (*lower surface*).—N77D.

*Winter leaf color.*—On upper and lower surface 200A.

*Petiole length.*—About 3.5 mm.

*Petiole diameter.*—About 1 mm.

*Petiole color.*—N186C.

*Pubescence.*—Stellate.

Flower description: Flowers are produced in April in Watkinsville, Ga. and sporadically until frost. An inflorescence is showy for about two weeks, and individual flowers last about two to three days and are self-cleaning. Flowers are lightly fragrant.

*Inflorescence type.*—Umbel consisting of 3 to 10 flowers produced from leaf axils and terminally.

*Inflorescence length.*—About 2.3 cm.

*Inflorescence width.*—About 3.1 cm.

*Peduncle.*—About 7.3 mm in length, about 1 mm in diameter, color is N186C, with stellate pubescence.

*Flower buds.*—Length: about 4 mm. Diameter: about 2 mm. Color: 184A.

*Calyx.*—About 3.5 mm in length, about 2 mm in diameter, color 184A upper and lower surface. Upper surface (outside): stellate pubescence. Lower surface (inside): glabrous.

*Sepals.*—Arrangement: opposite. Number: 4. Shape: ovate. Margin: entire. Apex: acute to obtuse, reflexed. Base: fused onto calyx cup. Length 0.32 cm. Width: 0.2 cm. Texture: pubescent. Color: upper surface — 64B; lower surface — 59C.

Petals:

*Arrangement/appearance.*—4 per flower.

*Petal length.*—About 1.7 cm.

*Petal width.*—About 1 mm.

*Petal shape.*—Strap-shaped.

*Petal apex*.—Acuminate.

*Petal margin*.—Entire.

*Texture*.—Smooth.

*Petal color*.—Upper and lower surfaces are 61B.

Stamens:

*Quantity/arrangement*.—4 or 5 stamens, 1.5 mm long, 0.3 mm in width, and N77A in color.

*Pollen*.—Produced in very small quantities and is 158A in color.

Pistils:

*Quantity*.—One or two inferior pistils per flower.

*Pubescence*.—None.

*Pistil length*.—About 2 mm in length.

*Pistil color*.—71A.

*Stigma*.—Rounded, 71A in color.

*Style*.—1 mm in length and 71A in color.

*Ovary*.—1 mm in length, 1 mm in diameter, and N80A in color.

Fruit:

*Type/appearance*.—Woody, two-valved, ovoid capsule.

*Length*.—6 mm.

*Diameter*.—4 mm.

*Mature color*.—200C. Each capsule contains two seeds that are about 5 mm long and 2 mm wide, and 200A in color. Five-year-old, original plant produced about 50 fruits.

Plant hardiness:

*Plant hardiness*.—USDA Hardiness Zone Map (2012): Zones 7-9.

Disease/pest resistance: Plants of claimed *Loropetalum* cultivar grown in the garden have not been noted to be susceptible or resistant to pathogens and pests common to *Loropetalum*.

I claim:

1. A new and distinct *Loropetalum chinense* var. *rubrum* plant named 'PIILC-I', substantially as illustrated and described herein.

* * * * *